(12) United States Patent
Soma et al.

(10) Patent No.: US 8,524,637 B2
(45) Date of Patent: Sep. 3, 2013

(54) COMPOSITION FOR CONTROLLING PESTS AND METHOD FOR CONTROLLING PESTS

(75) Inventors: Masato Soma, Narashino (JP); Atsushi Iwata, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/130,357

(22) PCT Filed: Nov. 24, 2009

(86) PCT No.: PCT/JP2009/070084
§ 371 (c)(1),
(2), (4) Date: May 20, 2011

(87) PCT Pub. No.: WO2010/061945
PCT Pub. Date: Jun. 3, 2010

(65) Prior Publication Data
US 2011/0230344 A1    Sep. 22, 2011

(30) Foreign Application Priority Data

Nov. 25, 2008  (JP) .................. 2008-299269

(51) Int. Cl.
*A01N 43/00*  (2006.01)
*A61K 31/41*  (2006.01)

(52) U.S. Cl.
USPC ......................... 504/139; 504/383

(58) Field of Classification Search
None
See application file for complete search history.

(56) References Cited

U.S. PATENT DOCUMENTS

| | | | |
|---|---|---|---|
| 5,256,679 A | 10/1993 | Minamida et al. | |
| 2003/0229087 A1 | 12/2003 | Mauler-Machnik et al. | |
| 2009/0143447 A1* | 6/2009 | Arthur et al. .................. | 514/370 |

FOREIGN PATENT DOCUMENTS

| | | |
|---|---|---|
| EP | 0 488 395 A1 | 6/1992 |
| JP | 4-202188 A | 7/1992 |
| JP | 5-271207 A | 10/1993 |
| JP | 2003-532654 A | 11/2003 |
| WO | WO 2006/024333 A1 | 3/2006 |
| WO | WO-2006024333 * | 3/2006 |
| WO | WO 2009/073164 A1 | 6/2009 |

OTHER PUBLICATIONS

International Search Report for PCT/JP2009/070084 dated Dec. 28, 2009.
English Translation of International Preliminary Report on Patentability for International Application No. PCT/JP2009/070084 dated Jul. 5, 2011.

* cited by examiner

*Primary Examiner* — Alton Pryor
(74) *Attorney, Agent, or Firm* — Birch, Stewart, Kolasch & Birch, LLP

(57) ABSTRACT

A pest controlling composition comprising clothianidin and metconazole as active ingredients.

5 Claims, No Drawings

COMPOSITION FOR CONTROLLING PESTS AND METHOD FOR CONTROLLING PESTS

TECHNICAL FIELD

The present invention relates to a pest controlling composition and a method of controlling pests.

BACKGROUND ART

There has hitherto been known, as an active ingredient of a pest controlling composition, clothianidin having an insecticidal activity and metconazole having a fungicidal activity (see, for example, The Pesticide Manual—14th edition (published by BCPC) ISBN 1901396142 (page 209, page 689)).

DISCLOSURE OF THE INVENTION

An object of the present invention is to provide a pest controlling composition having an excellent control activity against pests, and a method of controlling pests.

The present inventors have intensively studied and found that a control activity against pests is improved by using clothianidin and metconazole in combination, thus leading to the present invention.

That is, the present invention includes the following constitutions:

[1] A pest controlling composition comprising clothianidin and metconazole as active ingredients.
[2] The pest controlling composition according to [1], wherein the weight ratio of clothianidin to metconazole is within a range from 0.0125:1 to 500:1.
[3] A seed treating composition comprising clothianidin and metconazole as active ingredients.
[4] A plant seed which has been treated with clothianidin and metconazole as active ingredients.
[5] A pest controlling method, which comprises applying effective amounts of clothianidin and metconazole to plants or soil where plants are cultivated.
[6] Use of a combination of clothianidin and metconazole for controlling pests.

BEST MODE FOR CARRYING OUT THE INVENTION

Both clothianidin and metconazole in the present invention are known compounds and are described, for example, in "THE PESTICIDE MANUAL—14th EDITION (published by BCPC) ISBN 1901396142", page 209, page 689 and the like.

These compounds are obtained from commercially available formulations, or produced using a known method.

In a pest controlling composition according to the present invention, the weight ratio of clothianidin to metconazole is usually within a range from 0.0125:1 to 500:1, and preferably from 0.025:1 to 200:1. In the case of using as a spraying agent, the weight ratio is preferably within a range from 0.025:1 to 40:1. In the case of using as a seed treating composition, the weight ratio is more preferably within a range from 1:1 to 200:1.

The pest controlling composition according to the present invention may be those obtained by simply mixing clothianidin and metconazole, or usually may be those obtained by mixing clothianidin, metconazole and an inert carrier, optionally adding surfactants and other adjuvants for formulation, and formulating the obtained mixture into oil solutions, emulsifiable concentrates, flowable formulations, wettable powders, granular wettable powders, dust, granules and the like. The mixture can be formed into a formulation by a conventionally known procedure.

In the pest controlling composition according to the present invention, the total amount of clothianidin and metconazole is usually within a range from 0.1 to 99% by weight, preferably from 0.2 to 90% by weight, and more preferably from 1 to 80% by weight.

The inert carrier is exemplified by a solid carrier and a liquid carrier.

The solid carrier is in the form of fine powers, granules and the like. Examples of the material thereof include minerals such as kaolin clay, attapulgite clay, bentonite, montmorillonite, acid clay, pyrophyllite, talc, diatomite, and calcite; natural organic substances such as corncob powder and walnut shell powder; synthetic organic substances such as urea; inorganic salts such as calcium carbonate and ammonium sulfate; and synthetic inorganic substances such as synthetic hydrous silicon oxide.

Examples of the liquid carrier include aromatic hydrocarbons such as xylene, alkylbenzene, and methylnaphthalene; alcohols such as 2-propanol, ethylene glycol, propylene glycol, and ethylene glycol monoethyl ether; ketones such as acetone, cyclohexanone, and isophorone; vegetable oils such as soybean oil and cottonseed oil; petroleum-based aliphatic hydrocarbons; esters; dimethylsulfoxide; acetonitrile; and water.

Examples of the surfactant include anionic surfactants such as alkylsulfuric acid ester salt, alkylarylsulfonic acid salt, dialkylsulfosuccinic acid salt, polyoxyethylene alkylaryl ether phosphoric acid ester salt, lignin sulfonic acid salt, and naphthalenesulfonate polycondensed with formaldehyde; nonionic surfactants such as polyoxyethylene alkyl aryl ether, a polyoxyethylene-alkylpolyoxypropylene block copolymer, and sorbitan fatty acid ester; and cationic surfactants such as alkyltrimethyl ammonium salt.

Examples of the other adjuvant for formulation include water-soluble polymers such as polyvinyl alcohol and polyvinyl pyrrolidone; Arabian gum; alginic acid and a salt thereof; polysaccharides such as carboxymethyl cellulose (CMC) and xanthan gum; inorganic substances such as aluminum magnesium silicate and alumina sol; preservatives; colorants; and stabilizing agents such as isopropyl acidic phosphate (PAP) and BHT.

In the present invention, pests include noxious arthropods such as noxious insects and mites; nematodes; mollusks; and microorganisms which may cause plant diseases, such as mildew. Specific examples of the pests will be described below.

The pest controlling method of the present invention is a method of applying clothianidin and metconazole as active ingredients to pests, plants, or the soil where plants are cultivated.

In the above controlling method, it is possible to control pests and to protect plants from infestation due to pests by applying effective amounts of clothianidin and metconazole to pests, plants, or the soil where plants are cultivated.

In the present invention, the "effective amount" is an amount about the total of clothianidin and metconazole, and the amount of each compound may be an amount which exerts no effect in the case of applying only any one of compounds.

Examples of the above plants include foliage of plants, seeds of plants, and bulbs of plants. Herein, bulbs mean scaly bulb, solid bulb, root stock, stem tuber, root tuber, and rhizophore.

In the controlling method of the present invention, clothianidin and metconazole are usually applied as the pest controlling composition of the present invention from the viewpoint of ease and convenience at the time of application. Alternatively, they may be separately applied in the same period. Use of a combination of clothianidin and metconazole for the control of pests is also one aspect of the present invention.

Specific examples of the pest controlling method of the present invention include a treatment to foliage of plants, such as foliage spraying; a treatment to cultivation lands of plants, such as soil treatment; a treatment to seeds, such as seed disinfection or seed coating; and a treatment to bulbs, such as seed tuber.

Specific examples of the treating method to foliage of plants include a treating method of applying to surfaces of plants, such as foliage spraying and trunk spraying.

Examples of the soil treating method include spraying to the soil, soil incorporation, and irrigation of a chemical solution to the soil (irrigation of chemical solution, soil injection, and chemical solution drip).

The soil treatment is applied to planting hole, row, around a planting hole, around a row, entire surface of cultivation lands, ground side part of plants, interval between plants, under trunk, main trunk, earthing up, seedling raising box, seedling raising tray, and soil such as seedbed.

The treating period in the soil treatment can be appropriately set, for example, before seeding, at the time of seeding, immediately after seeding, raising period, before fix planting, at the time of fix planting, and rowing period after fix planting.

In the soil treatment, a solid fertilizer such as a paste fertilizer containing active ingredients may be applied to the soil. The soil treatment may also be carried out by application of an irrigation liquid mixed with active ingredients, such as injection into irrigation facilities (irrigation tube, irrigation pipe, sprinkler, etc.), mixing with an interrow inundation liquid, mixing with a water culture medium, and a spray treatment.

Examples of the method for a treatment to the seeds include a spray treatment in which a suspension of the pest controlling composition of the present invention is sprayed over seed surfaces or bulb surfaces in a mist form; a smearing treatment in which the pest controlling composition of the present invention is applied on seeds or bulbs; an immersion treatment in which seeds are immersed in a solution of the pest controlling composition of the present invention for a given time; a film coating treatment; and pellet coating treatment.

As described above, the pest controlling composition of the present invention can be used as a composition for the treatment to seeds, i.e. a seed treating composition. A seed treating composition containing clothianidin and metconazole as active ingredients, such as the pest controlling composition of the present invention is also one aspect of the present invention. Furthermore, a plant seed which has been treated with clothianidin and metconazole as active ingredients are one aspect of the present invention. To the plant seeds of the present invention, clothianidin and metconazole are usually applied in an effective amount. Therefore, plants grown from the plant seeds can control pests, and are also less likely to undergo plant diseases.

In the controlling method of the present invention, the application amount of clothianidin and metconazole varies depending upon the kind of plants to be treated, kind of pests to be controlled, degree of incidence of pests to be controlled, formulation, treatment period, meteorological conditions and the like. The total amount of clothianidin and metconazole (hereinafter referred to as an amount of the present active ingredient) is usually from 1 to 5,000 g, and preferably from 2 to 400 g, per 10,000 $m^2$ of the soil.

In the case of the emulsifiable concentrate, wettable powder, flowable formulation and the like, a treatment is usually carried out by spraying after diluting with water. In this case, the concentration of the present active ingredient is usually within a range from 0.0001 to 3% by weight, and preferably from 0.0005 to 1% by weight. In the case of the dust, granule and the like, a treatment is usually carried out as they are without being diluted.

In the treatment to seeds, the application is usually carried out in the amount of the present active ingredient within a range from 0.001 to 20 g, and preferably from 0.01 to 5 g, per kg of seeds.

The controlling method of the present invention can be used in crop lands or no-crop lands, such as upland field, paddy field, lawn and orchard.

The controlling method of the present invention can be used to control noxious arthropods, nematodes and the like of crop lands, where the following "plants" are cultivated, without undergoing chemical damage.

Agricultural crops: corn, rice, wheat, barley, rye, oat, sorghum, cotton, soybean, peanut, sarrazin, sugar beet, rapeseed, sunflower, sugar cane, tobacco and the like;

Vegetables: Solanaceae vegetables (eggplant, tomato, green pepper, hot pepper, potato, etc.), Cucurbitaceae vegetables (cucumber, pumpkin, zucchini, watermelon, melon, squash, etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese basil, mint, basil etc.), strawberry, sweat potato, yam, aroid etc.;

Ornamental flowers;

Ornamental foliage plant;

Lawns;

Fruit trees: pomaceous fruits (apple, common pear, Japanese pear, Chinese quince, quince etc.), stone fleshy fruits (peach, plum, nectarine, Japanese plum, yellow peach, apricot, prune etc.), citrus plants (Satsuma mandarin, orange, lemon, lime, grapefruit etc.), nuts (chestnut, walnut, hazel nut, almond, pistachio, cashew nut, macadamia nut etc.), berry fruits (blueberry, cranberry, blackberry, raspberry etc.), grape, persimmon, olive, loquat, banana, coffee, date, coconut etc.; and Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew).

The above "plants" also include those provided with resistance to HPPD inhibitors such as isoxaflutole; ALS inhibitors such as imazethapyr and thifen sulfuronmethyl; EPSP synthesis enzyme inhibitors such as glyphosate; glutamine synthesis enzyme inhibitors such as glufosinate; acetyl CoA carboxylase inhibitors such as sethoxydim; PPO inhibitors such as flumioxazin; and herbicides such as bromoxynil, dicamba, and 2,4-D, by way of a classical breeding method or a genetic engineering technology.

Examples of the "plants" having resistance given by a classic breeding method include rapeseed, wheat, sunflower and rice which are resistant to imidazolinone-based ALS inhibitor-type herbicides such as imazethapyr, and which have been already on the market under the trade name of Clearfield (registered trademark). Likewise, there is a soybean which has resistance to a sulfonyl urea-based ALS inhibitor-type herbicide such as thifen sulfuronmethyl similarly given by a classic breeding method, and which have been already on the market under the trade name of STS soybean. Likewise, there is SR corn as an example of a plant which has been provided with resistance to an acetyl CoA carboxylase inhibitor, such as triune oxime-based and aryloxy phenoxypropionic acid-based herbicides, by a classical breeding method. Examples of the plant provided with resistance to the acetyl CoA carboxylase inhibitor are described in Proc. Natl. Acad. Sci. USA, Vol. 87, pp. 7175-7179 (1990) or the like. Also, mutated acetyl CoA carboxylase, which is resistant to the acetyl CoA carboxylase inhibitor, is reported in Weed Science, Vol. 53, pp. 728-746 (2005). The plants with resistance to the acetyl CoA carboxylase inhibitor can be fabricated by introducing such a mutated acetyl CoA carboxylase gene into a plant by means of a genetic engineering technology, or by introducing resistance-providing mutation into acetyl CoA carboxylase of the plant, Further, by introducing base substitute mutagenesis nucleic acid into a plant cell or introducing site-specific amino acid substitute mutation to the acetyl CoA carboxylase gene and ALS gene of the plant using the technology represented by chimeraplasty technology (Gura T., Repairing the Genome's Spelling Mistakes, Science 285; 316-318 (1999)), plants with resistant to acetyl CoA carboxylase inhibitors and ALS inhibitors can be fabricated.

Examples of the plants having resistance given by a genetic engineering technology include corn, soybean, cotton, rapeseed and beet having resistance to glyphosate, which have already been on the market under the trade names of Roundup Ready (registered trademark), Agrisure GT, and the like. Likewise, corn, soybean, cotton and rapeseed cultivars having resistance to glufosinate given by a genetic engineering technology has already been on the market under the trade name of LibertyLink (registered trademark) or the like. Likewise, cotton having resistance to bromoxynil given by a genetic engineering technology has already been on the market under the trade name of BXN.

The above "plants" also include plants which made it possible to synthesize selective toxins known as genus *Bacillus*, using a genetic engineering technology.

Examples of the toxins expressed in such genetically modified plants include insecticidal proteins derived from *Bacillus cereus* and *Bacillus popilliae*; δ-endotoxins derived from *Bacillus thuringiensis*, e.g. Cry1Ab, Cry1Ac, Cry1F, Cry1Fa2, Cry2Ab, Cry3A, Cry3Bb1 or Cry9C, and insecticidal proteins such as VIP1, VIP2, VIP3 and VIP3A; insecticidal proteins derived from nematodes; toxins produced by animals, such as scorpion toxin, spider toxin, bee toxin and insect-specific neurotoxins; filamentous fungi toxins; plant lectins; agglutinin; protease inhibitors such as trypsin inhibitors, serine protease inhibitor, patatin, cystatin and papain inhibitors; ribosome-inactivating proteins (RIP) such as ricin, corn-RIP, abrin, rufin, sapolin and briodin; steroid metabolic enzymes such as 3-hydroxysteroid oxidase, ecdysteroid-UDP-glucosyltransferase and cholesterol oxidase; ecdysone inhibitors; HMG-COA reductase; ion channel inhibitors such as a sodium channel inhibitors and calcium channel inhibitors; juvenile hormone esterase; diuretic hormone acceptors; stilbene synthetase; bibenzyl synthetase; chitinase; and glucanase.

Examples of the toxins expressed in such genetically modified plants include hybrid toxins, partially deficient toxins and modified toxins of δ-endotoxin proteins, such as Cry1Ab, Cry1Ac, Cry1F, Cry1Fa2, Cry2Ab, Cry3A, Cry3Bb1, Cry9C, Cry34Ab or Crt35Ab and insecticidal proteins, such as VIP1, VIP2, VIP3 or VIP3A. The hybrid toxins are fabricated by a novel combination of the different domains of such proteins, using a genetic engineering technology. As a partially deficient toxin, Cry1Ab in which a part of amino acid sequence is deficient, is known. In modified toxins, one or more amino acids of a natural toxin are replaced.

Examples of such toxins and genetically modified plants capable of synthesizing such toxins are described in EP-A-0 374 753, WO 93/07278, WO 95/34656, EP-A-0 427 529, EP-A-451 878, WO 03/052073 and the like.

The toxins contained in such genetically modified plants impart resistance to insect pests of Coleoptera, insect pests of Hemiptera, insect pests of Diptera, insect pests of Lepidoptera, and Nematoda to the plants.

It has already been known that there are genetically modified plants containing one or more insecticidal pest-resistant genes and capable of expressing one or more toxins. Some of them are commercially available. Examples of such genetically modified plants include YieldGard (registered trademark) (corn cultivar expressing a Cry1Ab toxin), YieldGard Rootworm (registered trademark) (corn cultivar expressing a Cry3Bb1 toxin), YieldGard Plus (registered trademark) (corn cultivar expressing Cry1Ab and Cry3Bb1 toxins), Herculex I (registered trademark) (corn cultivar expressing phosphinothricin N-acetyltransferase (PAT) for imparting resistance to a Cry1Fa2 toxin and Glufosinate), NuCOTN33B (registered trademark) (cotton cultivar expressing a Cry1Ac toxin), Bollgard I (registered trademark) (cotton cultivar expressing a Cry1Ac toxin), Bollgard II (registered trademark) (cotton cultivar expressing Cry1Ac and Cry2Ab toxins), VIPCOT (registered trademark) (cotton cultivar expressing a VIP toxin), NewLeaf (registered trademark) (potato cultivar expressing a Cry3A toxin), NatureGard (registered trademark) Agrisure (registered trademark) GT Advantage (GA21 Glyphosate resistant property), Agrisure (registered trademark) CB Advantage (Bt11 corn borer (CB) property), and Protecta (registered trademark).

The above "plants" include those provided with a capacity of producing an anti-pathogenic substance having selective activity, using a genetic engineering technology.

As the anti-pathogenic substance, for example, PR proteins are known (PRPs, described in EP-A-0 392 225). These anti-pathogenic substances and genetically modified plants producing thereof are described in EP-A-0 392 225, WO 95/33818, EP-A-0 353 191 and the like.

Examples of anti-pathogenic substances expressed in such genetically modified plants include ion channel inhibitors such as sodium channel inhibitors and calcium channel inhibitors (KP1, KP4 and XP6 toxins produced by virus are known); stilbene synthase; bibenzyl synthase; chitinase; glucanase; PR proteins; and microorganism-producing anti-pathogenic substances such as peptide antibiotics, antibiotics having a heterocycle, protein factors relating to resistance against palant diseases (referred to as plant disease resistance gene, described in WO 03/000906). These anti-pathogenic substances and genetically modified plants producing thereof are described in EP-A-0 392 225, WO 95/33818, EP-A-0 353 191 and the like.

The above "plants" include those provided with useful traits, such as reformed oil component and enhanced amino acid content, using a genetic engineering technology. The plants are exemplified by VISTIVE (registered trademark) (low linolenic soybean with reduced linolenic acid content), high-lysine (high-oil) corn (corn with increased lysine or oil content) and the like.

The above "plants" further include stacked varieties, which are fabricated by combining useful traits such as the above classical herbicidal traits or herbicide resistant genes, insecticidal pest resistant genes, anti-pathogenic substance-producing genes, reformed oil components and enhanced amino acid contents.

The pest controlling composition according to the present invention can protect plants from infestation due to noxious arthropods (noxious insects, noxious mites and the like) and nematodes which cause infestation such as feeding and sucking to the above plants.

Examples of noxious arthropods and nematodes on which the pest controlling composition according to the present invention exert a control activity include:

Hemiptera; planthoppers such as *Laodelphax striatellus, Nilaparvata lugens*, and *Sogatella furcifera*, leafhoppers such as *Nephotettix cincticeps* and *nephottix virescens*, aphids such as *Aphis gossypii, Myzus persicae, Brevicoryne brassicae, Macrosiphum euphorbiae, Aulacorthum solani, Rhopalosiphum padi*, and *Toxoptera citricidus*, stink bugs such as *Nezara antennata, Riptortus clavetus, Leptocorisa chinensis, Eysarcoris parvus, Halyomorpha mista*, and *Lygus lineolaris*, whiteflies such as *Trialeurodes vaporariorum, Bemisia tabaci*, and *Bemisia argentifolii*, scales such as *Aonidiella aurantii, Comstockaspis perniciosa, Unaspis citri, Ceroplastes rubens*, and *Icerya purchasi*, lace bugs, suckers and the like;

Lepidoptera: Pyralidae such as *Chilo suppressalis, Tryporyza incertulas, Cnaphalocrocis medinalis, Notarcha derogata, Plodia interpunctella, Ostrinia furnacalis, Ostrinia nubilaris, Hellula undalis*, and *Pediasia teterrellus*, Noctuidae such as *Spodoptera litura, Spodoptera exigua, Pseudaletia separata, Mamestra brassicae, Agrotis ipsilon, Plusia nigrisigna*, Genus *Trichoplusia*, Genus *eliothis*, and Genus *Helicoverpa*, Pieridae such as *Pieris rapae*, Tortricidae such as Genus *Adoxophyes, Grapholita molests, Leguminivora glycinivorella, Matsumuraeses azukivora, Adoxophyes orana fasciata, Adoxophyes* SP., *Homona magnanima, Archips fuscocupreanus, Lydia pomonella*, Gracillariidae such as *Caloptilia theivora* and *Phyllonorycter ringoneella*, Carposinidae such as *Carposina niponensis*, Lyonetiidae such as Genus *Lyonetia*, Lymantriidae such as Genus *Lymantria* and Genus *Euproctis*, Yponameutidae such as *Plutella xylostella*, Gelechiidae such as *Pectinophora gossypiella* and *Phthorimaea operculella*, Arctiidae such as *Hyphantria cunea*, Tineidae such as *Tinea translucens* and *Tineola bisselliella*, and the like;

Thysanoptera: Thrips such as *Frankliniella occidentalis, Thrips parmi, Scirtothrips dorsalis, Thrips tabaci, Frankliniella intonsa*, and *Frankliniella fusca*, and the like;

Diptera; leafminer flies such as *Musca domestica, Culex popiens pallens, Tabanus trigonus, Hylemya antiqua, Hylemya platura, Anopheles sinensis, Agromyza oryzae, Hydrellia griseola, Chlorops oryzae*, and *Liriomyza trifolii, Dacus cucurbitae, Ceratitis capitata*, and the like;

Coleoptera: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*, and the like;

Orthoptera: *Locusta migratoria, Gryllotalpa africana, Oxya yezoensis, Oxya japonica*, and the like;

Hymenoptera; *Athalia rosae, Acromyrmex* spp., *Solenopsis* spp. and the like;

Blattodea: *Blattella germanica, Periplaneta fuliginosa, Periplaneta americana, Periplaneta brunnea, Blatta orientalis*, and the like;

Acarina: Tetranychidae such as *Tetranychus urticae, Panonychus citri*, and Genus *Oligonychus*, Eriophyidae such as *Aculops pelekassi*, Tarsonemidae such as *Polyphagotarsonemus latus*, Tenuipalpidae, Tuckerellidae, Acaridae such as *Tyrophagus putrescentiae*, Dermanyssidae such as *Dermatophagoides farinae* and *Dermatophagoides ptrenyssnus*, Cheyletidae such as *Cheyletus eruditus, Cheyletus malaccensis* and *Cheyletus moorei*, and the like; and Nematodes: *Aphelenchoides besseyi, Nothotylenchus acris*, and the like.

Preferred examples among the above noxious arthropods include aphids, thrips, leafminer flies (*Agromyza oryzae*), click beetle (*Agriotes* spp.), Colorado potato beetle (*Leptinotarsa decemlineata*), Japanese beetle (*Popillia japonica*), cupreous chafer (*Anomala cuprea*), boll weevil (*Anthonomus grandis*), rice water weevil (*Lissorhoptrus oryzophilus*), tobacco thrips (*Frankliniella fusca*), corn rootworms (*Diabrotica* spp.), Diamondback moth (*Plutella xylostella*), Small White (*Pieris rapae*) and soybean pod borer (*Leguminivora glycinivorella*).

By applying effective amounts of clothianidin and metconazole to plants or the soil where plants are cultivated as the pest controlling method of the present invention, it is possible to further control plant diseases.

The present application includes a plant disease controlling composition containing clothianidin and metconazole as active ingredients, and a plant disease controlling method which comprises applying effective amounts of clothianidin and metconazole to plants or the soil where plants are cultivated.

In the above plant disease controlling composition, the total amount of clothianidin and metconazole is usually within a range from 0.1 to 99% by weight, preferably from 0.2 to 90% by weight, and more preferably from 1 to 80% by weight. The above plant disease controlling composition can be prepared in the same manner as in the above pest controlling composition.

In the above plant disease controlling method, the application of clothianidin and metconazole can be carried out in the same manner as in the above pest controlling method.

The above plant disease controlling composition is also effective for the following plant diseases.

Diseases of rice: *Magnaporthe grisea, Cochliobolus miyabeanus, Rhizoctonia solani, Gibberella fujikuroi*.

Diseases of wheat: *Erysiphe graminis, Fusarium graminearum, F. avenacerum, F. culmorum, Microdochium nivale, Puccinia striiformis, P. graminis, P. recondita, Micronectriella nivale, Typhula* SP., *Ustilago tritici, Tilletia caries, Pseudocercosporella herpotrichoides, Mycosphaerella graminicola, Stagonospora nodorum, Pyrenophora tritici-repentis*.

Diseases of barley: *Erysiphe graminis, Fusarium graminearum, F. avenacerum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani* due to *Rhizoctonia* fungus.

Diseases of corn; *Ustilago maydis, Cochliobolus heterostrophus, Gloeocercospora sorghi, Puccinia polysora, Cercospora zeae-maydis, Rhizoctonia solani* due to *Rhizoctonia* fungus.

Diseases of citrus fruits: *Diaporthe citri, Elsinoe fawcetti, Penicillium digitatum, P. italicum, Phytophthora parasitica, Phytophthora citrophthora*.

Diseases of apple: *Monilinia mali, Valsa ceratosperma, Podosphaera leucotricha, Alternaria alternata* apple pathotype, *Venturia inaequalis, Colletotrichum acutatum, Phytophtora cactorum, Diplocarpon mali, Botryosphaeria berengeriana.*

Diseases of pear: *Venturia nashicola, V. pirina, Alternaria alternata* Japanese pear pathotype, *Gymnosporangium haraeanum, Phytophtora cactorum;*

Diseases of peach: *Monilinia fructicola, Cladosporium carpophilum, Phomopsis* SP.

Diseases of grape: *Elsinoe ampelina, Glomerella cingulata, Uncinula necator, Phakopsora ampelopsidis, Guignardia bidwellii, Plasraopara viticola.*

Diseases of persimmon: *Gloeosporium kaki, Cercospora kaki, Mycosphaerella nawae.*

Diseases of gourd: *Colletotrichum lagenarium, Sphaerotheca fuliginea, Mycosphaerella melonis, Fusarium oxysporum, Pseudoperonospora cubensis, Phytophthora* SP., *Pythium* SP.;

Diseases of tomato: *Alternaria solani, Cladosporium fulvum, Phytophthora infestans.*

Diseases of eggplant: *Phomopsis vexans, Erysiphe cichoracearum.*

Diseases of cruciferous vegetable: *Alternaria japonica, Cercosporella brassicae, Plasmodiophora brassicae, Peronospora parasitica.*

Diseases of gourd: *Puccinia allii, Peronospora destructor.*

Diseases of soybean: *Cercospora kikuchii, Elsinoe glycines, Diaporthe phaseolorum var. sojae, Septoria glycines, Cercospora sojina, Phakopsora pachyrhizi, Phytophthora sojae, Rhizoctonia solani* due to *Rhizoctonia* fungus.

Diseases of kidney bean: *Colletotrichum lindemthianum.*

Diseases of peanut: *Cercospora personata, Cercospora arachidicola, Sclerotium rolfsii.*

Diseases of pea: *Erysiphe pisi, Fusarium solani F. SP. pili.*

Diseases of potato: *Alternaria solani, Phytophthora infestans, Phytophthora erythroseptica, Spongospora subterranean f. sp. subterranea, Rhizoctonia solani.*

Diseases of strawberry: *Sphaerotheca humuli, Glomerella cingulata.*

Diseases of tea: *Exobasidium reticulatum, Elsinoe leucospila, Pestalotiopsis* SP., *Colletotrichum theaesinensis.*

Diseases of tobacco: *Alternaria longipes, Erysiphe cichoracearum, Colletotrichum tabacum, Peronospora tabacina, Phytophthora nicotianae.*

Diseases of rapeseed: *Sclerotinia sclerotiorum, Rhizoctonia solani* due to *Rhizoctonia* fungus.

Diseases of cotton: *Rhizoctonia solani* due to *Rhizoctonia* fungus.

Diseases of sugar beet: *Cercospora beticola, Thanatephorus cucumeris, Thanatephorus cucumeris, Aphanomyces cochlioides.*

Diseases of rose: *Diplocarpon rosae, Sphaerotheca pannosa, Peronospora sparsa.*

Diseases of chrysanthemum and Liliaceae vegetables: *Bremia lactucae, Septoria chrysanthemi-indici, Puccinia horiana.*

Diseases of various plants: diseases caused by *Pythium* fungus (*Pythium aphanidermatum, Pythium debarianum, Pythium graminicola, Pythium irregulars, Pythium ultimum*), *Botrytis cinerea, Sclerotinia sclerotiorum, Sclerotium rolfsii.*

Diseases of Japanese radish: *Alternaria brassicicola.*

Diseases of turf: *Sclerotinia homeocarpa,* Brown Patch disease, and *Rhizoctonia solani.*

Diseases of banana: *Mycosphaerella fijiensis, Mycosphaerella musicola.*

Diseases of sunflower: *Plasmopara halstedii.*

Seed diseases or diseases at the initial stage of the growth of various plants, caused by fungi of Genus *Aspergillus*, Genus *Penicillium*, Genus *Fusarium*, Genus *Gibberella*, Genus *Trichoderma*, Genus *Thielaviopsis*, Genus *Rhizopus*, Genus *Mucor*, Genus *Corticium*, Genus *Phoma*, Genus *Rhizoctonia*, the genus *Diplodia* and the like.

Viral diseases of various plants mediated by the genus *Polymixa*, the genus *Olpidium* or the like.

In the case the plant disease controlling composition of the present invention is used for a spray treatment, a high control effect is particularly expected on plant diseases that occur on wheat, barley, corn, soybean, cotton, rapeseed, grape, turf or apple among the above diseases. Examples of the disease on which a high activity is expected, among plant diseases that occur on these plants, include *Mycosphaerella graminicola, Pyrenophora tritici-repentis, Mycrodochium nivale, Rhizoctonia solani, Pseudocercosporella herpotrichoides, Pyrenophora teres, Cochliobolus sativus, Pyrenophora graminea, Ustilago tritici, U. nulla, Tilletia caries, Rhynchosporium secalis, Cochliobolus heterostrophus, Cercospora zeae-maydis, Cercospora kikuchii, Septoria glycines, Rhizoctonia solani, Rhizoctonia solani, Sclerotinia sclerotiorum, Botrytis cinerea, Sclerotinia homeocarpa, Rhizoctonia solani,* and *Venturia inaequalis.*

In the case the plant disease controlling composition of the present invention is used in a seed treatment, a high control effect is particularly expected on plant diseases that occur on corn, sorghum, rice, rapeseed, soybean, potato, sugar beet and cotton among the above plants. Examples of the disease, on which a high control effect is expected, among plant diseases that occur on these plants include *Rhizoctonia solani* caused by *Rhizoctonia* fungi, diseases caused by fungi of the genus *Pythium*, and diseases caused by fungi of the genus *Fusarium*.

EXAMPLES

The present invention will be described in more detail below by way of Formulation Examples, Seed Treatment Examples and Test Examples, but the present invention is not limited only to the following Examples. In the following Examples, parts are parts by weight unless otherwise specified.

Formulation Example 1

Twenty parts of clothianidin, 5 parts of metconazole, 1.5 parts of sorbitan trioleate and 28.5 parts of an aqueous solution containing polyvinyl alcohol (water:polyvinyl alcohol=26.5:2 in a weight ratio) are mixed and the obtained mixture is finely ground by a wet grinding method. Thereafter, 45 parts of an aqueous solution containing 0.05 parts of xanthan gum and 0.1 parts of aluminum magnesium silicate is added thereto and 10 parts of propylene glycol is further added, followed by stirring and mixing to obtain a flowable formulation.

Formulation Example 2

Material slurry is prepared by mixing 5 parts of clothianidin, 40 parts of metconazole, 5 parts of propylene glycol (manufactured by Nacalai Tesque, Inc.), 5 parts of Soprophor FLK (manufactured by Rhodia Nicca Co., Ltd.), 0.2 parts of Antifoam C Emulsion (manufactured by Dow Corning Corporation), 0.3 parts of Proxel GXL (manufactured by Arch Chemicals Inc.) and 49.5 parts of ion-exchange water. Glass beads (150 parts) ($\phi$=1 mm) are put in 100 parts of the slurry and the slurry is ground while cooling with cooling water for 2 hours. After grinding, glass beads are removed by filtration to obtain a flowable formulation.

Formulation Example 3

A granule is obtained by well grinding and mixing 1 part of clothianidin, 4 parts of metconazole, 1 part of synthetic hydrous silicon oxide, 2 parts of calcium lignin sulfonate, 30 parts of bentonite and 62 parts of kaolin clay, adding water, and well kneading the obtained mixture, followed by granulation and drying.

Formulation Example 4

A dust is obtained by well grinding and mixing 1 part of clothianidin, 2 parts of metconazole, 85 parts of kaolin clay and 10 parts of talc.

Formulation Example 5

Ten parts of clothianidin, 2.5 parts of metconazole, 1.5 parts of sorbitan trioleate, and 30 parts of an aqueous solution containing polyvinyl alcohol (water:polyvinyl alcohol=28:2 in a weight ratio) are mixed and the obtained mixture is finely ground by a wet grinding method. Thereafter, 47.5 parts of an aqueous solution containing 0.05 parts of xanthan gum and 0.1 parts of aluminum magnesium silicate is added thereto and 10 parts of propylene glycol is added, followed by stirring and mixing to obtain a flowable formulation.

Formulation Example 6

A wettable powder is obtained by well grinding and mixing 40 parts of clothianidin, 1 part of metconazole, 3 parts of calcium lignin sulfonate, 2 parts of sodium lauryl sulfate and 54 parts of synthetic hydrous silicon oxide.

Formulation Example 7

An emulsifiable concentrate is obtained by mixing 20 parts of clothianidin, 0.1 parts of metconazole and 79.9 parts of acetone.

Formulation Example 8

An emulsifiable concentrate is obtained by mixing 20 parts of clothianidin, 2 parts of metconazole and 78 parts of acetone.

Formulation Example 9

A flowable formulation is obtained by mixing 5 parts of clothianidin, 5 parts of metconazole, 35 parts of a mixture of white carbon and a polyoxyethylene alkyl ether sulfate ammonium salt (in the weight ratio of 1:1) and 55 parts of water, and finely grinding the obtained mixture by a wet grinding method.

Seed Treatment Example 1

Treated seeds are obtained by smearing 10 kg of corn dry seeds with 40 ml of the flowable formulation produced in accordance with Formulation Example 1 using a rotary seed treating machine (seed dresser, manufactured by Hans-Ulrich Hege GmbH).

Seed Treatment Example 2

Treated seeds are obtained by dust-coating 10 kg of corn dry seeds with 50 g of the dust produced in accordance with Formulation Example 1.

Seed Treatment example 3

Treated seeds are obtained by smearing 10 kg of soybean dry seeds with 50 ml of the flowable formulation produced in accordance with Formulation Example 2 using a rotary seed treating machine (seed dresser, manufactured by Hans-Ulrich Hege GmbH).

Seed Treatment Example 4

Treated seeds are obtained by dust-coating 10 kg of cotton dry seeds with 40 g of the dust produced in accordance with Formulation Example 4.

Seed Treatment Example 5

Treated seeds are obtained by smearing 5 g of cucumber seeds with 1 ml of the emulsifiable concentrate produced in accordance with Formulation Example 7 using a rotary seed treating machine (seed dresser, manufactured by Hans-Ulrich Hege GmbH).

Test Example 1

An emulsifiable concentrate was obtained by mixing clothianidin and metconazole.

In accordance with Seed Treatment Example 5, cucumber (Sagami Hanjiro) seeds were smeared with the emulsifiable concentrate using a rotary seed treating machine (seed dresser, manufactured by Hans-Ulrich Hege GmbH).

The obtained treated seeds were allowed to stand overnight and sown on the soil with which each plastic pot was filled and then covered with the soil mixed with *Rhizoctonia solani* cultured in a bran culture medium. While sprinkling, culture was conducted in a greenhouse. Seven days after seeding, the number of seeds not showing epicotyl emergence was checked and severity was calculated using Equation 1 shown below. Based on the severity, the control value was calculated using Equation 2.

For comparison, acetone solutions each having a predetermined concentration of clothianidin or metconazole were prepared by mixing each of clothianidin and metconazole with acetone, and the same test was carried out. The results are shown in Table 2.

$$\text{Severity} = (\text{number of seeds not showing epicotyl emergence}) \times 100 / (\text{total number of sown seeds}) \quad \text{Equation 1}$$

$$\text{Control value} = 100 \times (A-B)/A \quad \text{Equation 2}$$

A: Severity of plants of the chemical non-treated district
B: Severity of plants of the chemical treated district

| Amount of application per 100 kg of seeds | | Control |
|---|---|---|
| Clothianidin | Metconazole | value |
| 200 g | 1 g | 61 |
| 200 g | 0 g | 4 |
| 0 g | 1 g | 39 |

Test Example 2

In accordance with Seed Treatment Example 1, corn seeds are smeared using a rotary seed treating machine (seed dresser, manufactured by Hans-Ulrich Hege GmbH). The obtained treated seeds are allowed to stand overnight and sown on the soil which each plastic pot is filled with and then covered with the soil mixed with *Rhizoctonia solani* separately cultured in a bran culture medium. While sprinkling, culture is conducted in a greenhouse. Ten days after seeding, the number of seeds not showing epicotyl emergence is checked and severity is calculated using the aforementioned "Equation 1" and also the control value is calculated using the aforementioned "Equation 2". Excellent control effect can be obtained by this method.

Test Example 3

Soybean seeds are sown in each of polyethylene cups and grown until emergence of the first true leaf, and then about 20 foxglove aphids (*Aulacorthum solani*) are made parasititic thereto. A wettable powder of tolclofos-methyl and a wettable powder of clothianidin are respectively diluted with water, followed by tank mixing to prepare tank mix solutions each containing a predetermined concentration of tolclofos-methyl and clothianidin. One day after, the above spray liquid is sprayed over soybean seedlings in a proportion of 20 ml/cup. Six days after spraying, the number of foxglove aphids is checked and the control value is determined by the following equation:

Control value (%)={1−(Cb×Tai)/(Cai×Tb)}×10Q in the equation, symbols have the following meanings:

Cb: The insect number before treatment on non-treated district

Cai: The insect number in observation on non-treated district

Tb: The insect number before treatment on treated district

Tai: The insect number in observation on treated district

Test Example 4

Corn (Pioneer) seeds were smeared with the emulsifiable concentrate prepared in accordance with Formulation Example 8 in an amount of 5 µl per one seed in a 15 ml centrifuge tube. The obtained treated seeds were sown in a 1/10000 area Wagner pot. After growing in a greenhouse (at room temperature of 23° C.) for 12 days, five barley leaf. miners (*Rhopalosiphum padi*) were released. Seven days after release of insects, the number of barley leaf miners was checked.

As a result, the number of insects of the test district was suppressed and a satisfactory pest controlling effect was obtained.

Industrial Applicability

According to the present invention, it is possible to provide a pest controlling composition having a high activity, and a method capable of effectively controlling pests.

The invention claimed is:

1. A pest controlling composition comprising clothianidin and metconazole as active ingredients.

2. The pest controlling composition according to claim 1, wherein the weight ratio of clothianidin to metconazole is within a range from 200:1 to 500:1.

3. A seed treating composition comprising clothianidin and metconazole as active ingredients.

4. A plant seed which has been treated with clothianidin and metconazole as active ingredients.

5. A pest controlling method, which comprises applying effective amounts of clothianidin and metconazole to plants or soil where plants are cultivated to control fungi.

* * * * *